(12) United States Patent  
vonBerge

(10) Patent No.: US 10,297,018 B2
(45) Date of Patent: May 21, 2019

(54) METHOD OF DIGITALLY GRADING LEATHER BREAK

(71) Applicant: LEAR CORPORATION, Southfield, MI (US)

(72) Inventor: Robert vonBerge, Rochester Hills, MI (US)

(73) Assignee: LEAR CORPORATION, Southfield, MI (US)

( * ) Notice: Subject to any disclaimer, the term of this patent is extended or adjusted under 35 U.S.C. 154(b) by 0 days.

(21) Appl. No.: 15/650,430

(22) Filed: Jul. 14, 2017

(65) Prior Publication Data

US 2019/0017128 A1    Jan. 17, 2019

(51) Int. Cl.
*G06T 7/00*    (2017.01)
*C14B 17/00*    (2006.01)
*G01N 33/44*    (2006.01)

(52) U.S. Cl.
CPC .......... *G06T 7/0004* (2013.01); *C14B 17/005* (2013.01); *C14B 17/16* (2013.01); *G01N 33/447* (2013.01); *G06T 2207/30124* (2013.01)

(58) Field of Classification Search
CPC ... C14B 17/16; G01N 21/8903; G01N 33/447
USPC ....................................................... 382/111
See application file for complete search history.

(56) References Cited

U.S. PATENT DOCUMENTS

| | | |
|---|---|---|
| 3,067,609 A | 12/1962 | Bailey et al. |
| 4,481,616 A | 11/1984 | Matey |
| 6,157,730 A | 12/2000 | Roever et al. |
| 2004/0071895 A1 | 4/2004 | Winkler |
| 2009/0180122 A1 | 7/2009 | Federici |
| 2011/0045231 A1* | 2/2011 | Kajiwara .................. B32B 5/26 428/91 |
| 2012/0307969 A1* | 12/2012 | Kraus-Guentner ..... C14B 17/16 378/58 |
| 2013/0177215 A1 | 7/2013 | Campbell et al. |
| 2013/0239833 A1* | 9/2013 | Yiannakou ............... B41J 3/407 101/487 |
| 2014/0208902 A1 | 7/2014 | Gordon |

FOREIGN PATENT DOCUMENTS

| | | | | |
|---|---|---|---|---|
| DE | 19824304 A1 * | 12/1999 | ............... | C14B 1/28 |
| EP | 1077377 | 2/2001 | | |
| FR | 2864668 A1 * | 7/2005 | .......... | G06T 7/0004 |
| KR | 20030080288 | 10/2003 | | |

OTHER PUBLICATIONS

Keyence Corporation, Keyence High-speed 2D/3D Laser Scanner LJ-V7000 Series Manual, 32 pgs, 2014 Keyence Corporation.

\* cited by examiner

*Primary Examiner* — Justin P. Misleh
(74) *Attorney, Agent, or Firm* — Brooks Kushman P.C.

(57) ABSTRACT

A method and apparatus for grading leather based upon the size and spacing of the breaks in the leather. All or a portion of a hide is fed to a fixture that compresses a local area of the hide into a concave shape. The outer side of the hide is compressed and the inner side of the hide is expanded to cause breaks to be manifested in a local area. The local area of the hide is scanned with a digitizing profilometer that measures the depth of the breaks as the hide is fed through the fixture. The depth data measured by the digitizing profilometer is recorded by a controller. The depth data is then correlated with location data representing the local area scanned to develop a map of the break.

17 Claims, 5 Drawing Sheets

METHOD OF DIGITALLY GRADING LEATHER BREAK

TECHNICAL FIELD

This disclosure relates to a method of measuring, grading and sorting leather hides based upon digitized surface profile mapping of leather break characteristics of the hide.

BACKGROUND

Leather used in manufacturing products such as leather seats, leather trim and other applications is subjectively graded by visual inspection. Leather "break" is one of the characteristics that are evaluated. Break describes an effect of a loose fiber structure within the leather. Break is manifested on the surface of the leather when it conformed in a concave manner with respect to the top surface (otherwise known as the "grain" surface). The concave conformation is typically achieved by placing the leather, grain side up, into a "half-pipe" or into the cup of your hand. This conformation puts a compressive stress on the grain surface and an expansive stress on the bottom layer (known as the "flesh-side" of the leather). If the fiber structure within the leather is sufficiently loose rather than tightly entwined, the leather will "break" or form pleats on the surface. Leather is graded, in part, based upon the size of the breaks and spacing between breaks in the leather surface. The size of the break is compared to physical standards or photographs of different size break images. Errors in the subjective measurement can lead to customer complaints or reduced yields.

Different areas on a single hide may have different break gradings. For example, the stomach, and neck areas of a hide are sub-prime because they normally have loose fiber structure and larger breaks compared to prime areas such as the back and flanks of the hide. When pieces are cut from the hide by dies, waterjet cutting, or laser cutting, leather parts used in high visibility and high stress areas are cut from prime areas while some leather parts may be cut from areas having larger break ratings. The location and borders of the prime and sub-prime areas varies by age, gender, type of animal, from hide to hide and batch to batch of hides.

Prime areas are conservatively designated to avoid quality issues with some peripheral prime areas not being used for prime parts even though they are of sufficient quality. As a result, maximum utilization of the prime leather of the hides is not achieved and added material cost is incurred.

Hides are inspected and graded upon receipt. Batches having extensive large break areas are rejected or may be accepted with credits based upon the quality of the hide. Visual inspections of the hides are labor intensive and documenting the quality is difficult because of the subjective nature of the inspection process.

This disclosure is directed to solving the above problems and other problems as summarized below.

SUMMARY

According to one aspect of this disclosure, a method of grading leather based upon the size and spacing of the breaks in the leather. The method begins with the step of fixturing all or a portion of a hide to a fixture that conforms a local area of the hide into a concave shape with the grain side of the hide being compressed and the flesh of the hide being expanded to cause a break to be manifested. Scanning the local area of the hide is performed with a digitizing profilometer that measures the depth and width of the breaks as the hide is fed through the fixture. The resultant digital data can be processed in real time or stored for later analysis. The depth data is then related to the scanned hide position to develop a map of the leather break.

The method may further comprise analyzing the map by measuring a size of the spaces between the break and converting the size of the spaces to digital data. The data may be analyzed to identify the peaks and valleys in the local area. The distance between the break may be converted into wave form data and separated into distinct wave forms that are digitized to grade the local areas of the hide. The wave form data may be correlated to the location data to develop at least a partial map of the break of the hide.

According to another aspect of this disclosure, a machine is disclosed for inspecting a hide. The machine includes a shaping fixture that bends a local area of the hide to form a grain side surface of the hide into a concave shape and a flesh side of the hide into a convex shape. The digitizing profilometer measures the depth of a break as the hide is fed through the fixture to develop depth data. A controller records depth data and correlates the depth data with location data representing the local area scanned to develop at least a partial map of the break in the hide.

The controller may analyze the size of the spaces between the break and convert the size of the spaces to digital data. The controller may convert the size of the spaces by applying a mathematic analysis such as a Fourier transform of the data.

The controller may analyze the depth data to identify the peaks and valleys in the local area and measure a distance between either the peaks or the valleys to determine the distance between the breaks, and a grade may be assigned based upon the distance between the break in the local areas of the hide. The controller may analyze the distance between the break by converting the data into wave form data to separate the composite wave data into distinct wave forms that are digitized to grade the local areas of the hide. The controller may analyze the wave form data and correlate the data to the location data to develop a map of the break in different local areas of the hide.

The digitizing profilometer may be a laser surface profiler, for example, an optical confocal lens, a capacitance sensor, a fiber optic sensor, or an acoustic echo sensor.

The shaping fixture may have a transparent semi-cylindrical guide and the feed system may include a set of feed rollers that feed the hide around the semi-cylindrical guide that forms the hide surface into the concave shape. A set of pinch rollers may be used to pull the hide away from the semi-cylindrical guide. The digitizing profilometer may be used to scan the hide surface in the semi-cylindrical guide as the digitizing profilometer moves parallel to a cylindrical axis of the semi-cylindrical guide.

The shaping fixture may have a transparent cylindrical roller guide and the feed system may include at least one feed roller that feeds the hide around the roller guide that forms the hide surface into the concave shape. At least one pinch roller may pull the hide away from the cylindrical roller guide. The digitizing profilometer scans the hide surface as the hide is fed around the roller and as the digitizing profilometer moves parallel to a cylindrical axis of the cylindrical roller.

In another embodiment, the shaping fixture may include a set of feed rollers and a set of pinch rollers that form the hide surface into the concave shape. The digitizing profilometer may be used to scan the hide surface as the digitizing profilometer moves parallel to an axis of the concave shape.

The shaping fixture may have a concave semi-cylindrical groove and the feed system may include a set of feed rollers that feed the hide into the semi-cylindrical groove and an extractor roller that pulls the hide away from the semi-cylindrical groove. The semi-cylindrical groove may define a plurality of vacuum ports that are operatively connected to a source of vacuum that draws the hide surface into the concave shape. The digitizing profilometer may scan the hide surface as it moves substantially parallel to a cylindrical axis of the semi-cylindrical groove.

The above aspects of this disclosure and other aspects will be described below with reference to the attached drawings.

DETAILED DESCRIPTION

The illustrated embodiments are disclosed with reference to the drawings. However, it is to be understood that the disclosed embodiments are intended to be merely examples that may be embodied in various and alternative forms. The figures are not necessarily to scale and some features may be exaggerated or minimized to show details of particular components. The specific structural and functional details disclosed are not to be interpreted as limiting, but as a representative basis for teaching one skilled in the art how to practice the disclosed concepts.

Figure 1:
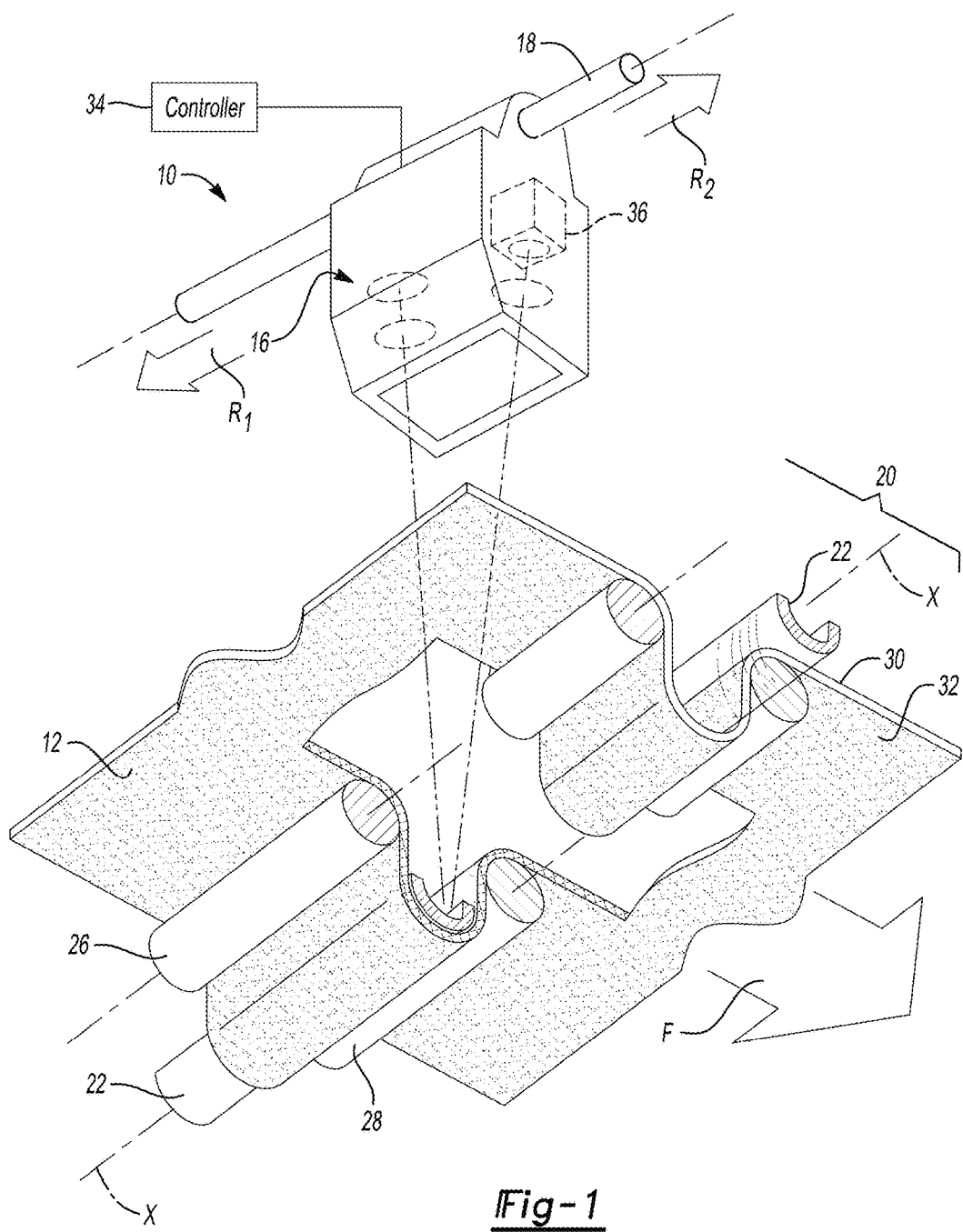
FIG. 1 is a fragmentary perspective view of a hide inspection machine for inspecting a hide to determine the size and spacing of break in the hide.

Referring to FIG. 1, an inspection machine is generally indicated by reference numeral 10 and is shown inspecting a hide 12. A digitizing profilometer 16 is oriented to inspect the hide 12 and is moved with the inspection machine 10 on a track 18, or rail, that traverses the hide 12 as the hide 12 is compressed in a shaping fixture 20.

Figure 2:
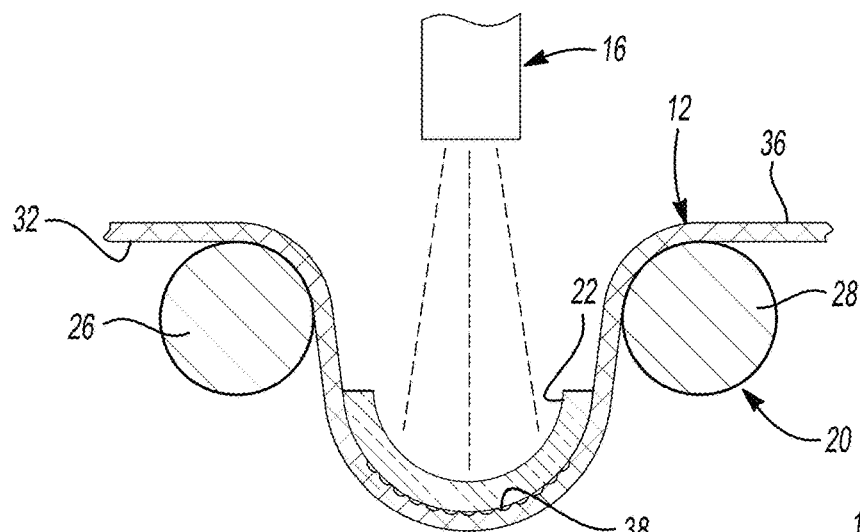
FIG. 2 is a fragmentary cross-section view of the hide inspection machine shown in FIG. 1 that has a laser for measuring the break in a hide as the hide is fed behind a transparent semi-cylindrical guide.

In the embodiment shown in FIGS. 1 and 2, the shaping fixture includes a transparent semi-cylindrical guide 22. The semi-cylindrical guide 22 is at least partially generated about a cylindrical axis X. The hide is fed in a feed direction F by a feed roller 26 to the semi-cylindrical guide 22 while the digitizing profilometer 16 scans the surfaced of the hide 12. The hide 12 has a grain surface 30, or outer surface, and a flesh surface 32, or inner surface. The grain surface 30 is scanned by the digitizing profilometer 16 as the hide 12 is fed around the semi-cylindrical guide 22.

A controller 34 receives digital data from a laser surface profiler 36 that can be processed in real time or stored for later analysis. The laser surface profiler 36 shown in FIGS. 1 and 2 may be used to scan the grain surface 30 of the hide 12. Alternatively, a laser surface profiler, such as an optical confocal lens, an acoustic echo profiler, a capacitance sensor, a fiber optic scanner, or the like may be selected as the laser surface profiler in the digitizing profilometer 16.

Referring to FIG. 2, the digitizing profilometer 16 scans the grain surface 30 of the hide 12 to detect break 38 in the leather hide 12. Break 38 becomes visible in the hide 12 when a local area 40 of the hide is compressed causing pleats to form on the surface. Leather may be graded based upon the size of the break 38 and spacing between pleats in the leather surface. The size of the break 38 is compared to physical standards or photographs of different size break images as will be explained with reference to FIGS. 11 and 12 below.

Figure 3:
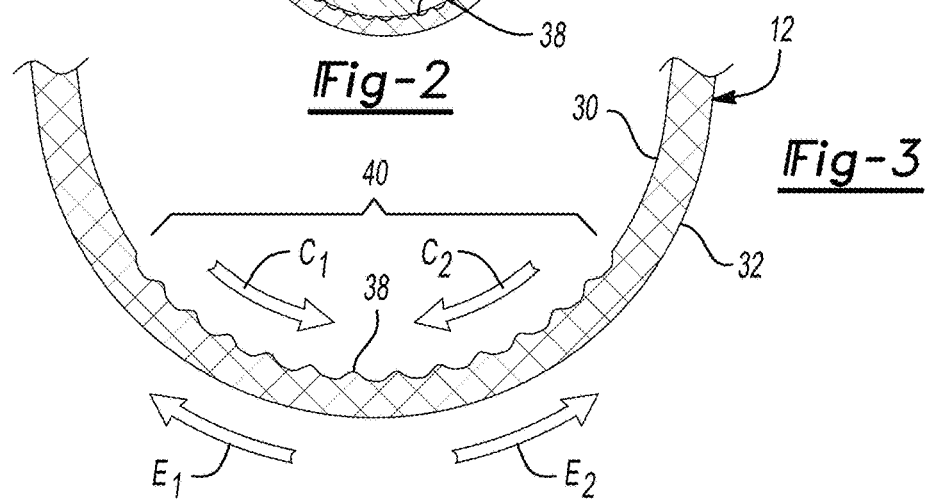
FIG. 3 is a diagrammatic view of a local area of a hide showing the hide surface being compressed into a concave shape and the flesh side of the hide being stretched into a convex shape.

Referring to FIG. 3, the hide 12 is shown with the local area 40 being compressed Arrows $C_1$ and $C_2$ show the grain side 30 of the hide 12 being compressed to show the size and spacing of the breaks 38. Arrows $E_1$ and $E_2$ show the flesh side 32 of the hide 12 being expanded, or stretched, while the grain side 30 of the hide 12 is compressed.

Figure 4:
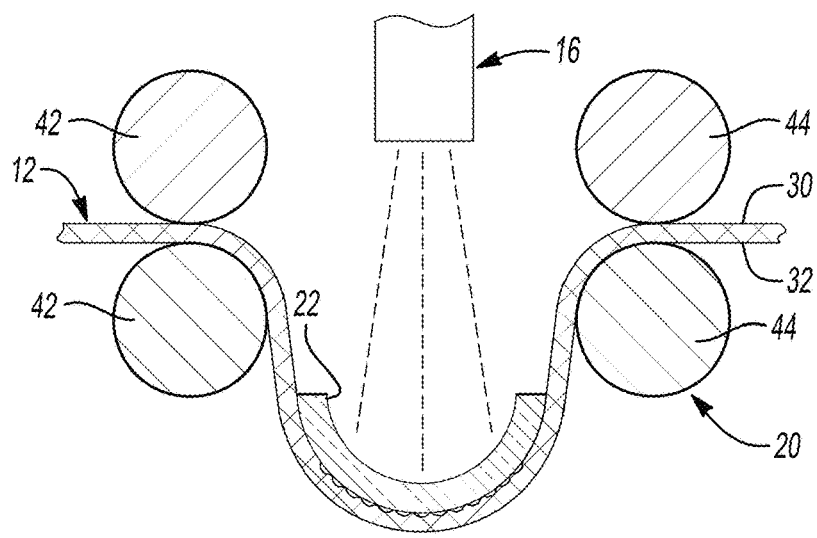
FIG. 4 is a fragmentary cross-section view of a hide inspection machine having a pair of feed rollers and a pair of pinch rollers that feed a hide past a laser that measures the breaks in the hide as the hide is fed behind a transparent semi-cylindrical guide.

Referring to FIG. 4, an alternative shaping fixture is illustrated that includes a pair of feed pinch rollers 42 and a pair of extraction pinch rollers 44 that feed the hide 12 into and pull the hide 12 out of the shaping fixture, respectively. The shaping fixture 20 includes the transparent semi-cylindrical guide 22. The grain surface 30 of the hide 12 is compressed as the hide 12 is drawn across the semi-cylindrical guide 22. The digitizing profilometer 16 scans the grain surface 30 through the semi-cylindrical guide 22 to inspect the hide 12 for break 38. The pinch rollers 42 and 44 provide positive control of the hide as it is routed around the semi-cylindrical guide 22.

Figure 5:
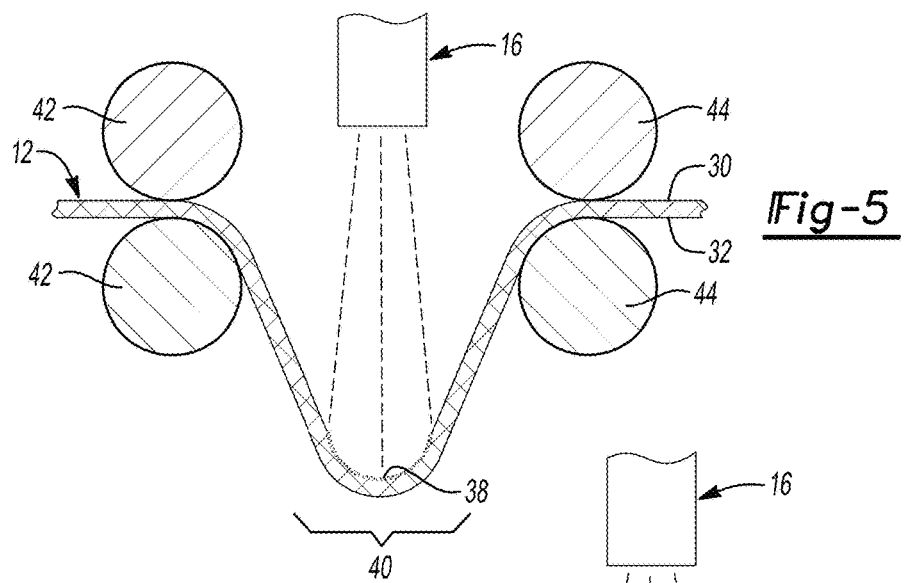
FIG. 5 is a fragmentary cross-section view of a hide inspection machine that has a pair of feed rollers and a pair of pinch rollers that feed a hide past a laser that measures the breaks in the hide side as the hide is folded into a concave configuration between the sets of rollers.

Referring to FIG. 5, an alternative shaping fixture is illustrated that includes feed pinch rollers 42 and extraction pinch rollers 44 that, respectively, feed the hide 12 into and pull the hide 12 out of the shaping fixture. The shaping fixture forms a compressed area in the local area 40 by controlling the rotational speed of the feed rollers 42 and the extraction rollers 44. The digitizing profilometer 16 scans the local area 40 the grain surface 30 of the hide 12 to detect break 38.

Figure 6:
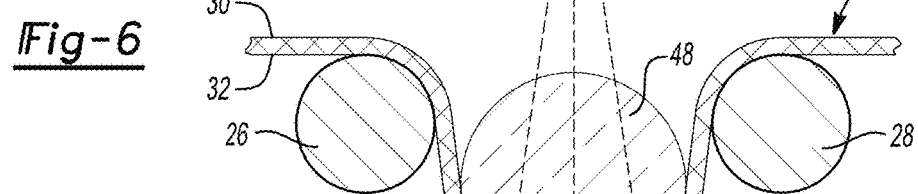
FIG. 6 is a fragmentary cross-section view of a hide inspection machine that has a feed roller and an extractor roller that feeds a hide past a laser that measures the breaks in the hide as the hide is fed behind a transparent roller.

Referring to FIG. 6, an alternative shaping fixture is illustrated that includes the feed roller 26 and the extraction roller 28 that feed the hide 12 into and pull the hide 12 out of the shaping fixture 20, respectively. The shaping fixture forms a compressed area in the local area 40 by partially wrapping the hide 12 around a transparent cylindrical roller 48. The digitizing profilometer 16 scans the local area 40 the grain surface 30 of the hide 12 as the hide 12 passes over the cylindrical roller 48 to detect break 38.

Figure 7:
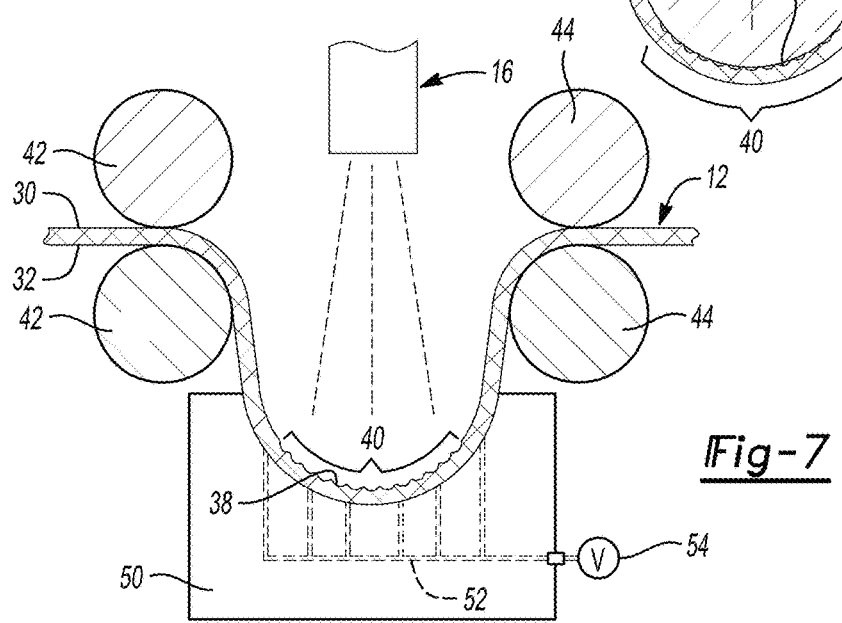
FIG. 7 is a fragmentary cross-section view of a hide inspection machine that has a pair of feed rollers and a pair of pinch rollers that feed a hide past a laser that measures the breaks in the hide as the hide is fed into a groove in the vacuum block that defines a plurality of vacuum ports that are operatively connected to a source of vacuum.

Referring to FIG. 7, an alternative shaping fixture is illustrated that includes the feed pinch rollers 42 and the extraction pinch rollers 44 that feed the hide 12 into and pull the hide 12 out of a vacuum guide block 50 that defines a concave groove. The shaping fixture forms a compressed area in the local area 40 by applying a vacuum through vacuum ports 52 defined by the vacuum guide block. Vacuum is provided from a source of vacuum 54, such as a vacuum pump, to the vacuum ports 52. The digitizing profilometer 16 scans the local area 40 the grain surface 30 of the hide 12 as the hide passes through the vacuum guide block 50 to detect the size and spacing of the break 38. While FIG. 7 discloses a vacuum block, it should also be understood that a guide block without vacuum ports could be used instead of the illustrated vacuum guide block 50. A simple guide block defining a concave groove would incorporate feed pinch rollers 42 and the extraction pinch rollers 44 that feed the hide 12 into and pull the hide 12 out of the concave groove.

Figure 8:
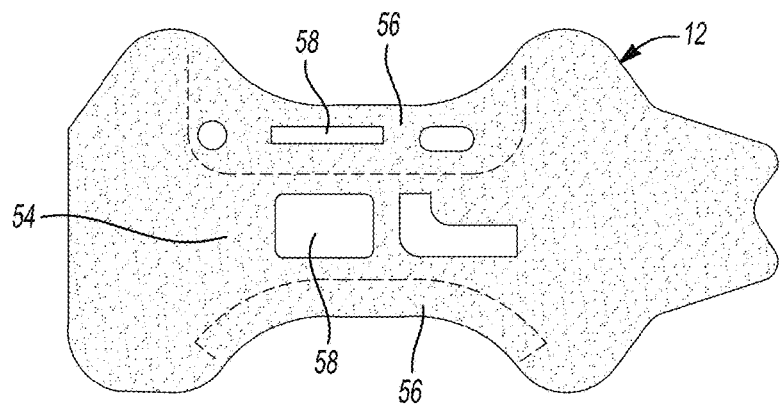
FIG. 8 is a plan view of a hide upon which a plurality of leather cutting dies are arranged.

Referring to FIG. 8 a hide 12 is diagrammatically illustrated to show prime areas 54 and sub-prime areas 56 of a typical hide. The back and flanks of the hide are normally characterized as having less break and pieces are cut out of these areas for seating surfaces, instrument panel areas, and the like because they require prime leather. The belly and neck areas are generally characterized a sub-prime areas and generally will have larger more spaced break 38.

Pieces, or blanks, are cut from the hide with dies 58 having knife edges (not shown) that are placed on the grain surface of the hide 12. The hide 12 with the dies 58 in position are then placed in a press that exerts pressure on the dies 58 to cut pieces in the desired shape from the hide 12.

Figure 9:
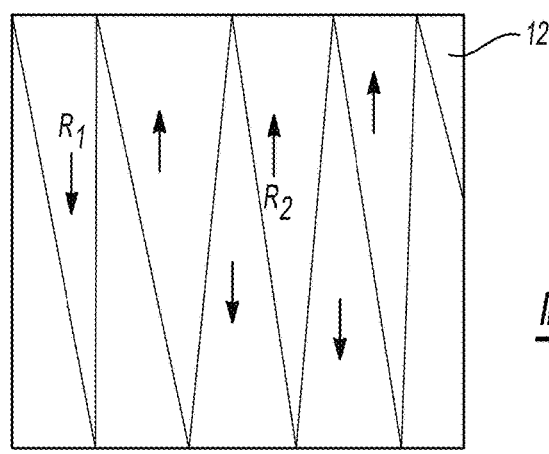
FIG. 9 is a diagrammatic view of a scanning pattern for scanning a complete hide.
Figure 10:
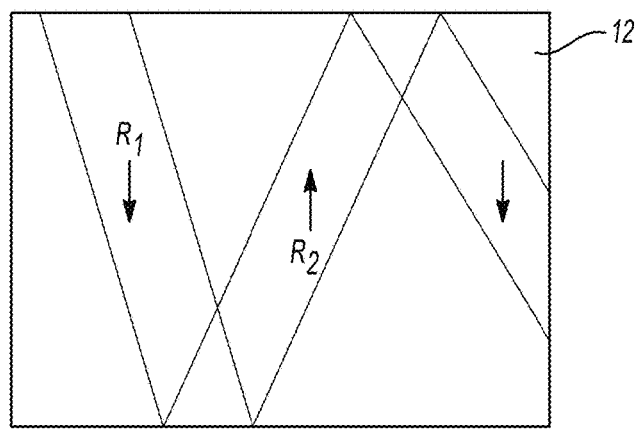
FIG. 10 is a diagrammatic view of a scanning pattern for partially scanning a hide.

Referring to FIGS. 9 and 10, two different approaches to scanning the hide 12 are illustrated. In FIG. 9 the entire surface of the hide 12 may be scanned and analyzed by controlling the rate that the hide 12 is fed through the shaping fixture 20 (shown in FIG. 1) and the speed at which the digitizing profilometer 16 traverses the rail 18. Parts of the scanning area are scanned twice as the digitizing profilometer 16 traverses the Hide 12 in the reciprocating directions $R_1$ and $R_2$. In FIG. 10 a partial scan of the hide 12 is performed to reduce the amount of data collected and provide a faster inspection process. The feed rate through the shaping fixture 20 is increased relative to the speed that the digitizing profilometer 16 traverses the hide 12.

Figure 11:
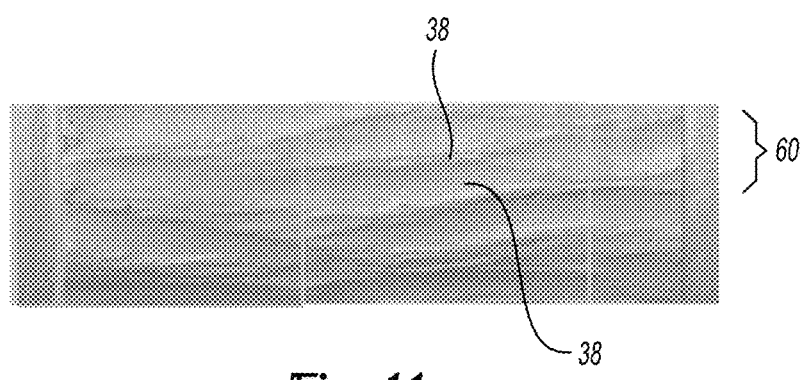
FIG. 11 is a digital image of a medium size break pattern.
Figure 12:
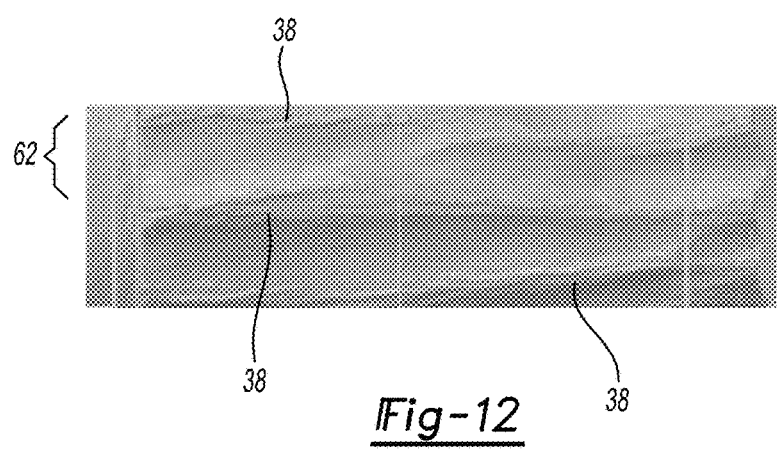
FIG. 12 is a digital image of a large size break pattern.

Referring to FIGS. 11 and 12, two examples of break are illustrated. In FIG. 11 a digital image of a medium size break 60 is illustrated. In FIG. 12 a digital image of a large size break 62 is illustrated. While different grading scales may be used. In one example, the hide 12 may be graded with grade 1 being quality leather having an average break size of 0.0-0.5 mm. Other grades of leather may be graded with grade 2 having an average break size of 0.5-1.0 mm; Grade 3 having an average break size of 1.0-1.5 mm; Grade 4 having an average break size of 1.5-2.0 mm; and Grade 5 having an average break size of more than 2 mm.

The embodiments described above are specific examples that do not describe all possible forms of the disclosure. The features of the illustrated embodiments may be combined to form further embodiments of the disclosed concepts. The words used in the specification are words of description rather than limitation. The scope of the following claims is broader than the specifically disclosed embodiments and also includes modifications of the illustrated embodiments.

What is claimed is:

1. A method of grading leather comprising:
   moving all or a portion of a hide through a fixture that compresses local areas of the hide into a concave shape with a grain side of the hide being compressed and a flesh side of the hide being expanded to cause a break to be manifested in the local areas;
   scanning the local areas of the hide with a digitizing profilometer that moves parallel to an axis of the concave shape to measure break size data in the local areas across the hide while moving the hide through the fixture;
   recording in a controller the break size data as measured by the digitizing profilometer across the hide; and
   analyzing in the controller the break size data to determine a grade for the local areas of the hide.

2. The method of claim 1 wherein the break size data includes data representing a space and depth between ridges of the break.

3. The method of claim 2 wherein the data representing the space and depth is used to determine the grade.

4. The method of claim 1 wherein the digitizing profilometer is a laser surface profile scanner.

5. The method of claim 1 wherein the digitizing profilometer is a capacitance sensor.

6. The method of claim 1 wherein the digitizing profilometer is a fiber optic sensor.

7. The method of claim 1 wherein the digitizing profilometer is an acoustic echo profiler.

8. A machine for measuring a hide for break comprising:
   rollers adapted to move the hide through the machine;
   a shaping fixture for conforming a local area of the hide to form a grain surface of the hide into a concave shape and a flesh surface of the hide into a convex shape;
   a digitizing profilometer for scanning the hide as the profilometer moves parallel to an axis of the concave shape wherein the profilometer measures a depth of a break as the hide is moved by the rollers through the shaping fixture to generate depth data in a plurality of local areas across the hide; and
   a controller for recording the depth data and analyzing the depth data to determine a grade for the plurality of local areas.

9. The method of claim 8 wherein the depth data includes data representing a space and depth between ridges of the break.

10. The method of claim 9 wherein the data representing the space and depth is used to determine the grade.

11. The machine of claim 8 wherein the digitizing profilometer is a laser surface profile scanner.

12. The machine of claim 8 wherein the digitizing profilometer is a capacitance sensor.

13. The machine of claim 8 wherein the digitizing profilometer is a fiber optic sensor.

14. The machine of claim 8 wherein the digitizing profilometer is an acoustic echo profiler.

15. The machine of claim 8
    wherein the shaping fixture has a transparent semi-cylindrical guide and the rollers include a set of feed rollers that feed the hide around the semi-cylindrical guide to form the hide into the concave shape and a set of pinch rollers that pull the hide away from the semi-cylindrical guide, and wherein the digitizing profilometer scans the hide through the semi-cylindrical guide.

16. The machine of claim 8
    wherein the shaping fixture has a transparent roller guide and the rollers include at least one feed roller that feeds the hide around the roller guide to form the hide into the concave shape and at least one extractor roller that pulls the hide away from the roller guide, and wherein the digitizing profilometer scans the grain surface as the hide is fed around the roller guide.

17. The machine of claim 8 wherein the shaping fixture has a concave groove and the rollers include a set of teed rollers that feed the hide into the concave groove and pinch rollers that pull the hide away from the concave groove, wherein the concave groove defines a plurality of vacuum ports that are operatively connected to a source of vacuum that draws the hide into the concave shape, and wherein the digitizing profilometer scans the hide in the concave groove.

* * * * *

UNITED STATES PATENT AND TRADEMARK OFFICE
CERTIFICATE OF CORRECTION

PATENT NO. : 10,297,018 B2
APPLICATION NO. : 15/650430
DATED : May 21, 2019
INVENTOR(S) : Robert vonBerge et al.

Page 1 of 1

It is certified that error appears in the above-identified patent and that said Letters Patent is hereby corrected as shown below:

In the Claims

Column 7, Line 8, Claim 17:
After "include a set of"
Delete "teed" and
Insert -- feed --.

Signed and Sealed this
Seventeenth Day of March, 2020

Andrei Iancu
*Director of the United States Patent and Trademark Office*